United States Patent
Oh et al.

(10) Patent No.: US 6,537,572 B1
(45) Date of Patent: Mar. 25, 2003

(54) PATCH TYPE ALUMINUM REMEDIAL IMPLEMENT

(76) Inventors: Dal-Hwan Oh, 119-102 Halla Vivaldi, Apt. 992-1 Daewon-Ri, Jori-Myun, Paju-City, Kyungi-do (KR); Seung Oh, 119-102 Halla Vivaldi, Apt. 992-1 Daewon-Ri, Jori-Myun, Paju-City, Kyungki-do (KR); Yong-Ju Wang, Hospital Sayworld, 153-8 Kansuk 2-Dong, Namdong-Ku, Inchon (KR); Do-Young Choi, 119-102 Halla Vivaldi, Apt. 992-1 Daewon-Ri, Jori-Myun, Paju-City, Kyungki-do (KR); Su-Youn Oh, 119-102 Halla Vivaldi, Apt. 992-1 Daewon-Ri, Jori-Myun, Paju-City, Kyungki-do (KR)

( * ) Notice: Subject to any disclaimer, the term of this patent is extended or adjusted under 35 U.S.C. 154(b) by 0 days.

(21) Appl. No.: 09/721,061

(22) Filed: Nov. 22, 2000

(30) Foreign Application Priority Data

Nov. 24, 1999 (KR) ............................................. 99-52490

(51) Int. Cl.$^7$ .............................. C25D 5/34; A61K 9/70
(52) U.S. Cl. ........................................ 424/449; 424/400
(58) Field of Search .......................... 205/202; 424/400, 424/449

(56) References Cited

U.S. PATENT DOCUMENTS 5,120,405 A * 6/1992 Ito et al. ..................... 205/202

* cited by examiner

Primary Examiner—Thurman K. Page
Assistant Examiner—Micah-Paul Young
(74) Attorney, Agent, or Firm—Fitch, Even, Tabin & Flannery

(57) ABSTRACT

A skin patch type aluminium alloy remedial implement, the implement of aluminium alloy (containing more than 99% of aluminium) including components in body fluid and inorganic bio elements, anodized but not processed with sealing treatment, wherein oxide coating formed thereon is microporous and functions as dielectric electrically and chemically, the coating being accumulated with negative potential to thereby possess a strong reduction potential, the strong reduction of the remedial implement leading to inorganic ion exchange and discharge of electrons accumulated on the oxide coating during contact with pain region of body, thereby controlling disorder of active potential at corresponding tissues and promoting normalization of ion pump among cell membranes for alleviation of pain.

3 Claims, No Drawings

PATCH TYPE ALUMINUM REMEDIAL IMPLEMENT

This application claims priority benefit to Republic of Korea application 1999-52490 filed on Nov. 24, 1999 under 35 U.S.C. § 119.

FIELD OF THE INVENTION

The present invention relates to a patch type aluminium alloy provided with a strong reduction potential and containing lots of inorganic bio element to control disorder of potential state in cells at a predetermined region of human body, thereby alleviating various pains and diseases.

BACKGROUND OF THE INVENTION

As a means of alleviating pains, physical method as well as drug have been developed in various forms. By way of example, Chinese medical systems have used methods where acupunture points are applied with needles or moxibustion to increase pain threshold. Recently electric needles are being used as needle material. Although acupuncture theraphy is known is for its apparent effect, no clear disclosure has been made on pain control mechanism thereof.

There are many known theories on mechanism of pain and edema of cell is regarded as one of many causes of pain. In the human body, material movement is realized in between cell walls by mechanism such as active transport, passive transport, osmosis pressure and the like.

At this time, when concentration gradient and electrical potential difference in and out of cell are dispersed or changed, a first edema of the cell is generated by moisture moving by way of osmosis.

The edema at the cell leads to changes in micro blood circulation and permeability of vessel wall. These kinds of phenomenon result in problem of micro blood circulation to thereby reduce active potential difference (membrane potential difference) of the cells. By way of example, membrane potential of normal cell is approximately (–) 60 mV~(–) 90 mV while that of damaged cell is about (–) 40 mV. The membrane potential of resting nerve cell is around (–) 70 mV and that of resting muscular cell is approximately (–) 90 mV while that of inflammatory cell is around (–) 120 mV.

The reduction of active potential difference generates inappropriate increase of hydrogen ions, leading to chemical change about the cells, which results in commencement of chemical reaction of inflammatory reaction. The inflammatory reaction causes stimulus to be transmitted to sensory receptive body, which is called a pain.

Under the above premise, there ware various approaches to treat the pain, and among the approaches, a fundamental method of removing a link leading to disease or pain by adjusting abnormal potential gradient of inner and outer membranes of a cell when the same occurs, can be thought of.

Meanwhile, attempts to treat pain by way of electric stimulus have been tried for a long time, most of these attempts are dynamic electric type methods calling for separated electric power devices.

There is a problem in the dynamic electric type method that prearrangement should be made on application to a predetermined region of voltage with regard to its intensity.

SUMMARY OF THE INVENTION

The present invention is disclosed to solve the aforementioned problems and it is an object of the present invention to provide a patch type aluminium remedial implement adapted to use an accumulated static electricity for removal of disadvantages involved with existing electric remedial implement, thereby adjusting abnormal potential gradient of cell membrane, which is a fundamental cause of pain and disease, to a normal state thereof.

It is another object of the present invention to provide a patch type aluminium remedial implement adapted to have a same or similar inorganic element composition as that of body fluid and manufactured with aluminium alloy having more than 99% of aluminium and not having a sealing treatment after anodization.

DETAILED DESCRIPTION OF THE INVENTION

Now, embodiments of the present invention will be described in detail with reference to manufacturing method and operational effect of the patch type aluminium remedial implement.

The remedial implement according to the present invention is characterized in that an aluminium alloy film having more than 99% of aluminium is anodized to form an oxide coating but is not gone through a typically applied sealing treatment to thereby allow maintaining a porous state.

When an aluminium metal film is anodized, a multitude of porosities are generated on surface thereof, and a separate sealing treatment is applied to seal the porosities. When the porous state remains uncorrected, aluminium is in the porosities contacts the oxygen to erode and continuously generate the process of oxidization although erosion thereof is very limited.

The aluminium alloy film contains various inorganic elements included in human body. Composition of inorganic elements is not particularly restricted but is appropriately selected according to the need. Manufacturing method of alloy follows the traditional alloy manufacturing style. A accumulated potential can be determined by adjustment of alloy composition.

With regard to function of inorganic elements, various metal ions of minute quantity take part in activation of various enzymes as composition elements of enzymes catalyzing the chemical reaction in an organism.

By way of example, a large quantity of ATP is consumed to maintain an electrical unbalanced state (potential difference) in between inner part and outer part possessed by a normal cell membrane, where enzymes involved in the ATP reaction are by and large activated by magnesium.

The remedial implement according to the present invention functions to emit or absorb corresponding ions when the essential inorganic elements in the living body are wanted or excessively generated, affecting disease of pain caused by abnormal control of corresponding inorgamic ions.

The aluminium alloy film thus manufactured is generally an insulator or a nonconductor due to alumina on the surface thereof, but the aluminium in the aluminium alloy therein becomes an aluminium positive ion ($Al^{3+}$) of electron-emitting nature, such that the inner aluminium alloy maintains a relatively high state of negative potential (reduction potential) compared with the alumina oxide coating.

Furthermore, the aluminium alloy according to the present invention is so electricity-storaged as to have a strong reduction potential, such that this force serves to act as electromotive force when touched with the living body, and the oxide coating functions as dielectric, such that half cell reaction occurs respectively at each half portion where the aluminium alloy and organ are separated. Current is generated at both side until electrical equilibrium is reached when elements in the metal element in the organ and the aluminium alloy are made of the same kind.

At this time, the porosities function as ion passages of other inorganic ions within the aluminium alloy, and when both sides electrically reach equilibrium, that is, when concentration of predetermined ions in the body cells reaches a normal state, the ions are stopped in moving.

The aluminium alloy according to the present invention consists of the same inorganic elements as those contained in the body, such that the aluminium alloy according to the present invention contacting skin comprises one system with body fluid as electrolyte where discharge or absorption of static electricity is freely generated according to potential difference.

Furthermore, between the aluminium alloy plate according to the present invention and body, the alumina coating works as dielectric and when the aluminium alloy plate touches the skin, static electricity is increased capacity-wise.

The touch leads to pressure and thermal electromotive force effect to generate electric charge in the body according to the electrostatic conduction and to finally cause to generate a discharge at one side.

At this time, it is not the simple electron movement that occurs but inorganic elements in the aluminium alloy is ionized to be absorbed into the body when the remedial implement according to the present invention touches skin of human body, or conversely, the ions of inorganic elements in the body fluid can be absorbed into the alloy.

Accordingly, it is possible that ions of inorganic elements wanted by the body can be supplied into the body from the alloy within the implement, such that potential can be controlled by the electrons and ion exchange of inorganic elements as well.

If pain itself can be explained by disorder of electric state in neuro-muscular cells (abnormalty of $Na^+$ and $K^+$ concentration), pain symptom can be removed by concentration gradient of ions about cell membranes by attaching the implement according to the present invention to a predetermined pain region.

In manufacturing the present implement, kind of inorganic bio elements and content thereof contained in the alloy can vary to a degree according to disease, and it should be noted that the present invention cannot be restricted according to composition thereof and kinds of contained elements.

A manufactured example and clinical example according to the present invention are given as below:

An aluminium alloy having a chemical composition ratio (%) (JIS 1050) of Si 0.25, Fe 0.04, Cu 0.04, Mn 0.04, Mg 0.05, Zn 0.05, Ti 0.03 and A§§99.5 is anodized to obtain a coating, and tests were performed on potential of the alloy plate with a predetermined size of copper plate as reference point in saline solution of 0.9% as an electrolyte. Control (diameter 10 mm, thickness 0.4 mm of Cu) and specimen of the present invention were tested nine times according to the aforementioned testing method. (Test date: Oct. 20, 1998~Nov. 3, 1998, test result issued by Korea Electric/Electronic Test Institute, Issued Number: Eu98-1228). The average values were +179.0 mV for control and ¤©465.3 mV for specimen of the present invention.

It was ascertained that the specimen according to the present invention shows a negative potential relative to the cooper plate.

The aluminium implement according to the present invention was directly performed on patients feeling great pains.

A. Selection of Disease Group

Patients suffering from back pain and arthralgia were selected at an Oriental hospital and attached with the aluminium implements at regions as large as possible applying non-woven fabric band aids to pain areas without administering any drugs or pills.

Kinds diseases and the number of opatients performed are as followings:
1. degenerative arthritis: 60 cases
2. degenerative spondylosis accompanied by sciatica: 30 cases
3. lumbar disc: 10 cases
4. back pain: 10 cases
5. frozen shoulder: 20 cases
6. bone fracture sequela: 5 cases
7. nicking synovitis: 5 cases
8. trunkal neutalgia by osteoporosis: 20 cases B. Duration the Implements were Attached
1. in case of back pain: average 12 days
2. Arthritis: average 12 days
3. Sciatica: average 7 days C. Result Approximately 70% of the subjective patients recovered from severe pains and about 10% of patients thereof reported that pains felt in every day lives disappeared.

About half of the patients complaining of general back pains reported that pangs were a little bit aggravated for 3~5 days of attachment of the implements according to the present invention but were gone or stayed only as dull symptoms thereafter.

As apparent from the foregoing, there is an advantage in the patch type aluminium remedial implement according to the present invention thus described in that only attachment thereof at pain or disease region can control lack of inorganic bio elements in the body or disorder of ion concentration in neuro cells, thereby healing various pains and disease regions at a low cost and safe way.

What is claimed is:

1. A method effective for alleviating pain comprising applying a remedial aluminum alloy patch to a portion of a body in need of pain alleviation, the remedial aluminum alloy patch comprising an aluminum alloy that includes more than about 99% aluminum, and more than one of an inorganic bio-element selected from the group consisting of Si, Fe, Cu, Mn, Mg, Zn, Ti, Ni, Mo, Na, K, Ca, B, and V.

2. The method of claim 1 wherein the aluminum alloy is artificially anodized with no sealing treatment.

3. The method of claim 1 wherein the remedial aluminum alloy patch wherein the inorganic bio-elements are the same as the inorganic bio-elements occurring in body fluids of a subject body.

* * * * *